United States Patent
Edberg

(10) Patent No.: US 9,512,462 B2
(45) Date of Patent: Dec. 6, 2016

(54) METHOD FOR DETECTING THE PRESENCE OR ABSENCE OF AN ANTIBIOTIC RESISTANT PATHOGENIC STAPHYLOCOCCI IN A TEST SAMPLE

(75) Inventor: Stephen C. Edberg, Longboat Key, FL (US)

(73) Assignee: Pilots Point LLC, Sarasota, FL (US)

( * ) Notice: Subject to any disclaimer, the term of this patent is extended or adjusted under 35 U.S.C. 154(b) by 0 days.

(21) Appl. No.: 14/357,489

(22) PCT Filed: Nov. 10, 2011

(86) PCT No.: PCT/US2011/060223
§ 371 (c)(1),
(2), (4) Date: Aug. 4, 2014

(87) PCT Pub. No.: WO2013/070230
PCT Pub. Date: May 16, 2013

(65) Prior Publication Data
US 2014/0349325 A1  Nov. 27, 2014

(51) Int. Cl.
*C12Q 1/14* (2006.01)
*C12Q 1/56* (2006.01)

(52) U.S. Cl.
CPC . *C12Q 1/14* (2013.01); *C12Q 1/56* (2013.01); *G01N 2333/31* (2013.01); *G01N 2333/952* (2013.01)

(58) Field of Classification Search
None
See application file for complete search history.

(56) References Cited

U.S. PATENT DOCUMENTS

| | | | | | |
|---|---|---|---|---|---|
| 5,380,652 | A * | 1/1995 | Ayres | .................. | C12Q 1/04 424/49 |
| 8,268,580 | B2 * | 9/2012 | Edberg | .................. | C12Q 1/14 435/34 |
| 8,524,468 | B2 * | 9/2013 | Edberg | .................. | C12Q 1/04 435/34 |
| 8,546,103 | B2 * | 10/2013 | Edberg | .................. | C12Q 1/14 435/36 |
| 2009/0191577 | A1 * | 7/2009 | Edberg | .................. | C12Q 1/14 435/13 |
| 2011/0027823 | A1 * | 2/2011 | Edberg | .................. | C12Q 1/14 435/36 |
| 2011/0256583 | A1 * | 10/2011 | Edberg | .................. | 435/34 |
| 2011/0269160 | A1 * | 11/2011 | Edberg | .................. | C12Q 1/14 435/13 |
| 2011/0269163 | A1 * | 11/2011 | Edberg | .................. | C12Q 1/14 435/23 |
| 2014/0147871 | A1 * | 5/2014 | Edberg | .................. | C12Q 1/14 435/13 |
| 2014/0295473 | A1 * | 10/2014 | Edberg | .................. | C12Q 1/14 435/18 |

FOREIGN PATENT DOCUMENTS

WO    WO 2011/119739    *  9/2011

OTHER PUBLICATIONS

Wertheim et al. "Improved Detection of Methicillin-Resistant Staphylococcus Aureus Using Phenyl Mannitol Broth Containing Aztreonam and Ceftizoxine", Journal of Clinical Microbiology, vol. 39, No. 7, Jul. 1, 2001.
Carey et al. "The Combined Oxacillin Resistance and Coagulase (CORC) Test for Rapid Identification and Prediction of Oxacillin Resistance in Staphyloccus Species Directly from Blood Culture", Journal of Clinical Pathology, vol. 61, No. 1, Jul. 1, 2008.
Supplementary European Search Report for EP 11875504 dated Jun. 10, 2015.

* cited by examiner

*Primary Examiner* — Ralph Gitomer
(74) *Attorney, Agent, or Firm* — O'Shea Getz P.C.

(57) ABSTRACT

A method for detecting the presence or absence of an antibiotic resistant pathogenic *staphylococci* in a test sample is provided. The method includes the steps of: a) providing a test medium having at least one hydrolysable substrate, which substrate is operable to promote the growth of the antibiotic resistant pathogenic *staphylococci* and to produce a detectable signal when the hydrolyzable substrate is metabolized by the antibiotic resistant pathogenic *staphylococci*; b) forming a mixture of the test sample and hydrated test medium; c) incubating the mixture at temperatures in the range of about 20° C. to about 35° C.; and d) detecting the presence or absence of the antibiotic resistant pathogenic *staphylococci* in the test sample by the presence or absence of the detectable signal in the mixture.

9 Claims, 2 Drawing Sheets

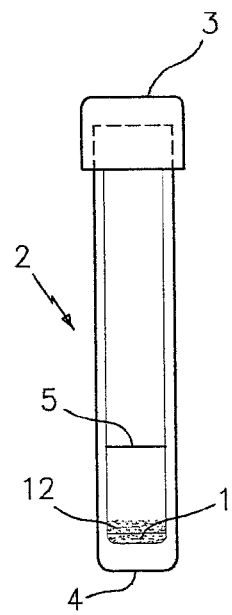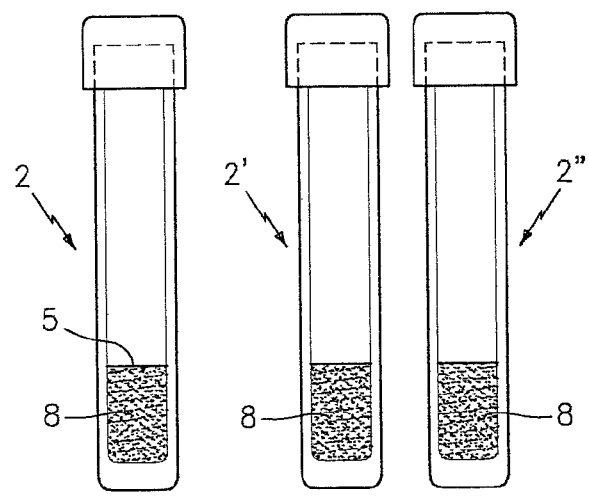
FIG. 1  FIG. 2
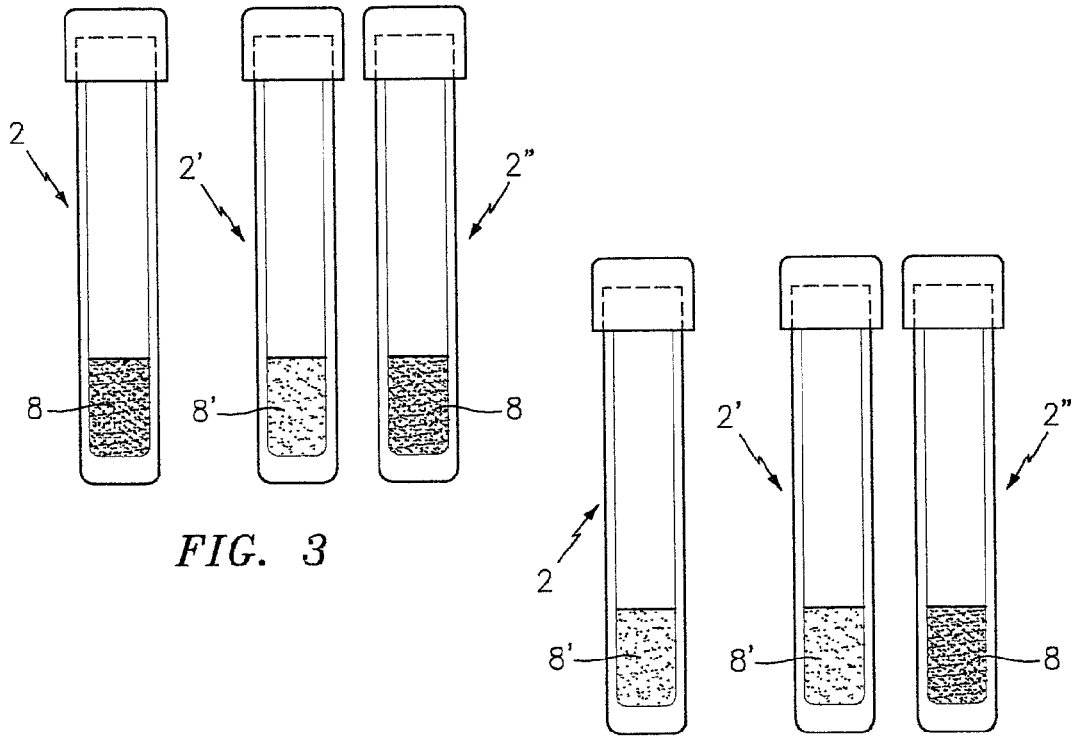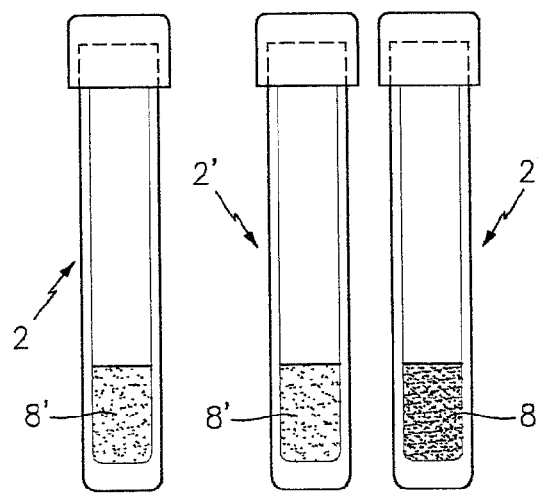
FIG. 3  FIG. 4

METHOD FOR DETECTING THE PRESENCE OR ABSENCE OF AN ANTIBIOTIC RESISTANT PATHOGENIC STAPHYLOCOCCI IN A TEST SAMPLE

BACKGROUND OF THE INVENTION

1. Technical Field

The present method and testing medium relate to the detection of pathogenic *staphylococci*, such as *Staphylococcus aureus* ("*S. aureus*") in a biological, environmental, or food sample, and more particularly to those methods and testing media utilizing reacting factors with which the targeted microbe(s) can produce one or both of a detectable signal in a hydrated mixture of the medium and sample being tested.

2. Background Information

Pathogenic *staphylococci* ("*P. staphylococci*") can be a virulent pathogen of animals and humans. Moreover, it can cause severe food poisoning by the production of a toxin. Diseases caused by *P. staphylococci* cover a very wide clinical spectrum, from simple skin infections to life threatening infections of the bones, heart, and organs. Of particular concern is the recognition that *P. staphylococci* infection is common after surgery. It is also associated with intravenous tubing and other implants.

The bacterium *P. staphylococci* may be transmitted between healthy individuals by skin to skin contact, or from a commonly shared item or a surface (e.g., tanning beds, gym equipment, food handling equipment, etc.) where the transfer may be made to a subsequent person who uses the shared item or touches the surface. Of great medical concern is the recognition that healthy people entering hospitals may "carry" *P. staphylococci* bacteria (e.g., on their skin, or in their noses, etc.) without any signs or symptoms that they do so. In the presence of favorable conditions (often found in, but not limited to, hospitals), the *P. staphylococci* bacteria can activate and cause serious infection. In addition, *P. staphylococci* bacteria can also be a source of food poisoning, often caused by a food handler contaminating the food product (e.g., meat, poultry, eggs, salads containing mayonnaise, bakery products, dairy products, etc.).

*P. staphylococci* bacteria is often, but not always, classified based on an individual clone's susceptibility to the class of antibiotics such as methicillin; e.g., methicillin susceptible *S. aureus* (MSSA), and methicillin resistant *S. aureus* (MRSA). Methicillin is a narrow spectrum beta-lactam antibiotic of the penicillin class. Until only a few years ago, MRSA was most commonly found in hospitals. Now, it is frequently also present in the noses, skin, etc. of people in the non-hospital community. Moreover, these MRSA bacteria are increasingly causing serious infections in the community. MRSA is particularly serious because only very few antibiotics (e.g., vancomycin) have been shown to be uniformly effective against MRSA. Vancomycin-resistant *Staphylococcus aureus* is another class of *P. staphylococci* bacteria. Vancomycin-resistant *Staphylococcus aureus* refers to strains of *S. aureus* that have become resistant to the glycopeptide antibiotic vancomycin. With the increase of *staphylococcal* resistance to methicillin, vancomycin (or another glycopeptide antibiotic; e.g., teicoplanin) is often used to treat infections with methicillin-resistant *S. aureus* (MRSA). Three classes of vancomycin-resistant *S. aureus* have emerged that differ in vancomycin susceptibilities: vancomycin-intermediate *S. aureus* (VISA), heterogenous vancomycin-intermediate *S. aureus* (hVISA), and high-level vancomycin-resistant *S. aureus* (VRSA). Other classes of *P. staphylococci* bacteria are associated with antibiotics including: linezolid, clindamycin, erythromycin, tetracycline, and sulfa-trimethoprim.

The Center for Disease Control and Prevention actively surveys for the development of MRSA. In 2000, the Society for Healthcare Epidemiology of America guidelines recommended contact isolation for patients with MRSA. In addition to the morbidity and mortality caused by MRSA, it has been estimated that each case of infection costs at least $23,000. Accordingly, many hospitals and nursing homes proactively sample patients for MRSA. See Clany, M., Active Screening in High-Risk units is an effective and cost-avoidant method to reduce the rate of methicillin-resistant *Staphylococcus aureus* infection in the hospital, Infection Control and Hospital Epidemiology 27: 1009-1017, 2006.

Meyer et al. (U.S. Pat. No. 4,035,238) describes the use of a broth for the detection of *S. aureus* that utilizes mannitol as a source of carbon and DNA meth. Neither of these chemicals are coagulase reactive substrates.

Rambach (U.S. Pat. No. 6,548,268) employs at least two chromogenic agents in an agar medium: 5-bromo-6-chloro-indoxyl-phosphate; and 5-bromo-4-chloro-3-indoxyl glucose in the presence of desferoxamine. An individual colony hydrolyzing these substrates will produce colors that will mix with each other and not be independent of one another.

A large number of classical culturing procedures are utilized to detect MSSA and MRSA from samples collected from humans, animals, food, etc. The culturing procedures share a basic medium (e.g., a trehalose-mannitolphosphatase agar) with chemical inhibitors such as 6-8% sodium chloride, potassium tellurite, and a variety of antibiotics; See Stevens, D. L. and Jones, C., "Use of trehalose-mannitol-phosphatase agar to differentiate *Staphylococcus epidermidis* and *Staphylococcus saprophyticus* from other coagulase-negative *staphylococci*", J. of Clin. Microbiology 20:977-980, 1984. The use of mannitol as a carbon source and salt as a selective agent into an agar known as mannitol-salt agar has been commonly used in clinical laboratories; See Baird, R. M. and Lee, W. H., "Media used in the detection and enumeration of *Staphylococcus aureus*., Int. J. Food Microbiology. 26:209-211, 1995. Within the prior art of culturing, it is a generally accepted procedure to perform coagulase tests utilizing samples of *S. aureus* that are isolated in a pure culture as a required test to achieve sufficient specificity.

The procedure "*S. aureus* 10", available from bioMérieux, Inc., Durham, N.C., USA, uses an alpha-glucosidase substrate in agar to detect *S. aureus*. A single substrate is utilized; See Perry, J. D. et al., "Evaluation of *S. aureus* 10, a new chromogenic agar medium for detection of *Staphylococcus aureus*", J. Clin. Microbiology 41: 5695-5698, 2003. A variant of this medium, which contains added antibiotics and sodium chloride, is designed to detect MRSA; See Perry et al., "Development and evaluation of a chromogenic agar medium for methicillin-resistant *Staphylococcus aureus*", J. of Clin. Micro. 42: 4519-4523, 2004.

Selepak and Witebsky disclose a study evaluating the inoculum size and lot-to-lot variability of the tube coagulase test for *S. aureus*. Specimens were collected and isolates were generated from the bacterial colonies on agar plates. Tubes containing anticoagulated rabbit coagulase plasma were inoculated with a part of, or more than one, *staphylococcal* colony from the isolates. The tubes were incubated and examined for the presence of clot. According to Selepak and Witebsky "with some isolates and some lots of coagulase plasma, even a single colony [from the isolate] may not provide enough inoculum for a positive coagulase test". Furthermore, Selepak and Witebsky state that "[e]xpressed more quantitatively, at least $10^8$ organisms per ml should be used whenever possible for each coagulase tube test. Our data further suggests that *S. aureus* does not grow in coagulase plasma; therefore, the incubation of coagulase plasma for 18 to 24 h does not compensate for the use of small inoculum." Thus, Selepak and Witebsky indicate that it is impractical, if not impossible, to detect the presence or absence of *S. aureus* in first generation biological specimen samples using a direct coagulase test. See Selepak, S. T et al, "Inoculum Size and Lot-to-Lot Variation as Significant Variables in the Tube Coagulase Test for *Staphylococcus aureus*", *Journal of Clin. Microbiology*, November 1985, p. 835-837]

Orth and Anderson disclose the use of a mannitol coagulase agar for the detection of *S. aureus*. The disclosure technique detects *S. aureus* by a fibrin deposition around the colony, and does not disclose a technique wherein detection is predicated on the formation of a gel. In addition, the technique is used to detect all stains of *S. aureus* indiscriminately. See, Orth, D. S. and Anderson, A. W., "Polymyxin—Coagulase—Mannitol—Agar", Applied Microbiology, January 1970, pp. 73-75.

It would, therefore, be desirable to provide a test mixture and a method that can rapidly detect a targeted antibiotic resistant strain of *P. staphylococci* directly from a first generation sample, one that does not require a skilled technician to perform the method, one that does not require the use of isolates developed from the specimen sample (i.e., one that can be performed on a "first generation" specimen sample) but one that can be used on such isolates, one that does not require a large concentration of *S. aureus* organisms to be accurate, and one that is stable at room temperatures for an extended time period.

SUMMARY OF THE INVENTION

This invention relates to a method and test medium for detection of specific strains of antibiotic resistant *P. staphylococci* bacteria in a biological (e.g., human or animal), environmental, or food sample. Examples of types of antibiotic resistant *P. staphylococci* include, but are not limited to, methicillin resistant *S. aureus* (MRSA), methicillin susceptible resistant *S. aureus* (MSSA), vancomycin resistant *S. aureus* (VRSA), etc.

According to an aspect of the present invention, a method for detecting the presence or absence of a targeted strain of antibiotic resistant *P. staphylococci* in a test sample is provided. The method includes the steps of: a) providing a test medium having at least one hydrolysable substrate, which substrate is operable to promote the growth of the targeted strain of antibiotic resistant *P. staphylococci* and to produce a detectable signal when the hydrolysable substrate is metabolized by the targeted strain of antibiotic resistant *P. staphylococci*; b) forming a mixture of the test sample and hydrated test medium in the test tube; c) incubating the mixture at temperatures in the range of about 20° C. to about 42° C.; and d) detecting the presence or absence of the targeted strain of antibiotic resistant *P. staphylococci* in the test sample by the presence or absence of the detectable signal in the mixture in the tube. The detectable signal will typically be produced within 6-8 hours after inoculation of the medium with the sample.

According to another aspect of the present invention, a test medium for detecting the presence or absence of a targeted strain of antibiotic resistant *P. staphylococci* in a test sample is provided. The test mixture includes an amount of amino acids, an amount of nitrogen sources, an amount of salts, an amount of vitamins, an amount of calcium, and at least one hydrolysable substrate. The substrate is operable to promote the growth of the targeted strain of antibiotic resistant pathogenic *staphylococci* and to produce a detectable signal when the hydrolyzable substrate is metabolized by the targeted strain of antibiotic resistant *P. staphylococci*.

In some embodiments, the present invention utilizes a medium that includes coagulase substrates (sometimes referred to as "coagulase reacting factors"), that react specifically with the enzyme coagulase produced by *P. staphylococci* (e.g., *S. aureus*) to form a clot, as well as constituents that facilitate multiplication of the *P. staphylococci* (i.e., "growth promoting constituents"). The enzyme coagulase is specific to pathogenic *staphylococci*, as is disclosed in the Code of The Federal Register, Title 21, Chapter 1, Sub Part C, Sec. 866.2160 "Coagulase Plasma".

In some embodiments, the present invention utilizes a combination of the above described mediums operable to detect one or more targeted strains of antibiotic resistant *P. staphylococci*. The combination of the detectable signal and the clot, via the constituents that create those aspects in the presence of a targeted strain of antibiotic resistant *P. staphylococci*, synergistically produce a test and with increased specificity to the targeted bacteria. The coagulase reaction (i.e., the clot) increases the efficiency of the sensing of the detectable signal. One of the reasons the efficiency is increased is because the solid/quasi-solid matrix (which may be a gel, etc.) formed by the coagulase reaction allows for a more efficient metabolism of the hydrolysable substrates. Another reason the efficiency is increased is because the solid/quasi-solid matrix creates a lowered oxygen tension, which enhances the glycolytic pathway of catabolism (e.g., splits sugars and digests them more efficiently). The containment of the hydrolysable substrates within the clot inhibits the access to oxygen which in turn promotes anaerobic fermentation and consequent product of more detectable colors. The detectable signal will typically be produced within 6 to 8 hours after inoculation of the medium with the sample.

The present medium is preferably prepared in a form that facilitates handling, packaging, storing, etc., of the medium. A dry powder that can be hydrated into liquid form is a particularly preferable embodiment of the test medium, but the present invention is not limited to a powder form. The medium may assume a liquid form, or any other form (e.g., paste, gel, etc.), preferably one that can be hydrated for use.

The growth promoting constituents within the test medium that facilitate the multiplication of and sustain *P. staphylococci* can be varied to suit the application. Those in the art will recognize that many different combinations of constituents, and varying relative amounts of the same constituents, can be used to provide the same functionality. Constituents that promote the growth of *P. staphylococci* include, but are not limited to: a) sources of nitrates and proteins; b) materials operative to assist in the generation of nucleic acid synthesis; c) sources of energy for the *P. staphylococci*; d) sources of amino acid growth factors; and in some embodiments, e) materials operable to help repair damaged target organisms. This list of growth promoting constituents does not represent all of the materials that can be beneficial within the medium, but does illustrate materials that are acceptable (e.g., vitamins, salts, minerals, inorganic moieties, etc.). The medium may include other constituents that benefit the performance of the test.

In most applications of the present invention, it will be desirable to utilize a medium that includes the following: a) an effective amount of one or more amino acids; b) an effective amount of one or more nitrogen sources; c) an effective amount of one or more salts; d) an effective amount of one or more vitamins; e) an effective amount of calcium; and f) an effective amount of a hydrolyzable substrate, such as one or more sugars that can be metabolized by the target bacteria. Those skilled in the art will recognize that natural sources of amino acids can be used rather than pure sources of amino acids. The natural sources (e.g. extract of whole organisms, such as yeast) may be in a mixture form or in a purified form. Natural sources in mixture form can contain varying amounts of amino acids and vitamins. Those skilled in the art will further recognize that many different combinations of amino acids and vitamins can be used in the present invention test mixture.

For those embodiments of the present invention operable to produce a clot in the presence of the targeted strain of antibiotic resistant *P. staphylococci*, the medium further includes coagulase substrates (sometimes referred to as "coagulase reacting factors"), that react specifically with the enzyme coagulase produced by *P. staphylococci* (e.g., *S. aureus*) to form a clot. The coagulase substrates within the test mixture may be provided within plasma, or may be provided by another substance that is operative to react with the coagulase produced by *S. aureus* to form a clot. Present testing indicates that rabbit plasma is a favorable source of a coagulase substrate. Other plasmas (e.g., pork plasma) may be used alternatively. Fibrinogen is another example of a source of a coagulase substrate. Bovine fibrogen is an acceptable type of fibrogen for use in the present invention. In those embodiments that utilize plasma as a source of a coagulase substrate, it may be preferable to add a non-plasma source of a coagulase substrate to the test mixture to ensure an adequate source of coagulase substrate within the test mixture. As an example, our testing indicates that combining fibrinogen and rabbit plasma within the test mixture is an effective means for ensuring a consistent, adequate source of coagulase substrates. An advantage of adding a material such as fibrinogen to the test mixture is that it increases the performance consistency of the test mixture, and makes the method less susceptible to variability that may occur with plasma.

The term "effective amount" as used herein to describe an amount of a constituent within the present medium, means an amount that is sufficient to carry out the function associated with that particular constituent. As indicated herein, constituents within the medium may be varied in an amount depending upon the particular other constituents within that configuration of the medium; e.g., a lesser amount of a particular constituent may be an "effective amount" in medium configurations wherein other constituents provide part of the function that could have been provided by the particular constituent.

The hydrolysable substrate includes nutrient molecules which, when metabolized by the targeted strain(s) of antibiotic resistant *P. staphylococci* produce a detectable signal; e.g., the visible color of the solution (or other detectable signal) containing the specimen is changed as a result of the nutrient being metabolized by the target bacteria. For example, the hydrolysable substrate can include a natural sugar (e.g., mannitol, trehalose, etc.) having one or more monosaccharides joined with an indicator moiety that does not produce a detectable signal when joined with the natural sugar. When the nutrient is metabolized by the target bacteria and the bond between the nutrient and the indicator moiety is broken, the indicator moiety produces a sensible signal (e.g., becomes colored—visible yellow). In those embodiments wherein the indicator moiety is operable to produce a color change, the indicator moiety can produce color in the visible range, ultraviolet range, or the infrared range, although color in the visible range facilitates test analysis in many cases.

Those in the art will further recognize that carbon, nitrogen, trace elements, vitamins, amino acids and selective agents can be provided in many forms. Generally, it is preferred to have an amount of vitamins and amino acids within a predetermined range, but those in the art will recognize that the actual properties of each ingredient may be varied so that reduction in the amount of one ingredient can be compensated by an increase in the amount of another. This is particularly relevant when the amino acids, trace elements, or vitamins essential to the growth of the target microbes are known. Some ingredients may be provided in reduced amounts or deleted if they may be synthesized endogenously by the microorganism whose presence is to be determined. Salts may be provided as a source of ions upon dissociation.

In some embodiments, effective amounts of drug ingredients which selectively inhibit the growth of one or more non-targeted strains of *P. staphylococci* (e.g., MSSA) present in the sample are also included in the test medium.

The test medium may be packaged in a container (e.g., a test tube, a container with a flat bottom wall, etc.) that facilitates the testing process. If the medium is prepared in a form that can be hydrated, the mixture can be hydrated with sterile water or non-sterile water.

To detect the presence of a targeted antibiotic resistant strain of *P. staphylococci* within a sample, the sample is obtained from a biological (e.g., human or animal), environmental, or food specimen. Embodiments of the present invention can be configured to permit analysis of first generation samples, and other embodiments configured to be capable of analyzing first and later generational samples. First generational test samples can be collected by a variety of different techniques; e.g., a human or animal sample can be collected by wiping a swab within the nose of a subject. Nasal swabs are a particularly convenient way of collecting a test sample, but they are not the only collection method; e.g., test samples can be collected from throat swabs, skin lesions, undamaged skin, etc. Likewise, first generational food samples can be collected from the food itself, or wiping food residue from surfaces in contact with the food, etc. Once a first generational sample is collected directly from the source specimen (e.g., the biological, environmental, or food specimen), the sample is inoculated directly into the present medium; there is no need to cultivate second or later generation bacterial colonies off of an agar plate prior to analysis of the sample as is typically done for those analyses that can only be used with second or later generational samples. The sensitivity of the present invention is adequate to detect first generational samples. Embodiments of the present invention can, however, be used to analyze second or later generation samples.

The inoculated sample is incubated under conditions favorable to facilitate the multiplication of the targeted antibiotic resistant strain of *P. staphylococci*. In the case of a powdered test medium hydrated with water, the incubation may be carried out at temperatures between about 20° C. to 35° C. The combination of sequential enzyme specificity, and enhancing growth factors specific to the targeted antibiotic resistant strain of *P. staphylococci*, provides multiple hurdles which prevent the competing non-target bacteria from being detected within the test period; e.g., a period of 24 hours or less.

The present invention testing medium and method can be used in hospital admissions, routinely in intensive care units, in nursing homes, dialysis patients, people receiving home immunosuppressive therapy, and the like. It can also be used in environmental settings (e.g., gyms, tanning salons, restaurants, etc.) where the *P. staphylococci* may be transferred from a human carrier and it can be used to test various different foods for *P. staphylococci* contamination. It will be appreciated that a substantial benefit of the present method and mixture is that they may be performed/used without the need for expensive equipment or skilled medical technologists, Another substantial benefit of the present method/mixture is that it is operative to detect a relatively small amount of *P. staphylococci* in the test sample; e.g., the present method/mixture has detected MRSA in samples having concentrations of MRSA as low as 100-1000 CFU/ml.

For those embodiments of the present invention that distinguish MRSA from MSSA, the medium may include useful constituents such as anti-ribosomal amino glycoside antibiotics, including gentamicin, kanamycin, tobramycin, and sisomicin, that inhibit growth of MSSA, but not MRSA.

BRIEF DESCRIPTION OF THE DRAWINGS

FIG. 1 is a side elevational view of a test tube containing a dry test mixture which is to be used in detecting the presence or absence of the targeted strain of *P. staphylococci* using the present invention.

FIG. 2 is a side elevational view of a set of three test tubes of the type shown in FIG. 1 after the test mixture in each tube has been hydrated.

FIG. 3 is a side elevational view of the set of test tubes of FIG. 2 after the test has been performed on a sample specimen, wherein the sample specimen has been found to be free of the targeted *P. staphylococci*.

FIG. 4 is a side elevational view of the set of test tubes of FIG. 2 after the test has been performed on a sample specimen, wherein the sample specimen has been found to contain the targeted *P. staphylococci*.

DETAILED DESCRIPTION OF SPECIFIC EMBODIMENTS OF THE INVENTION

Figures 5, 6:
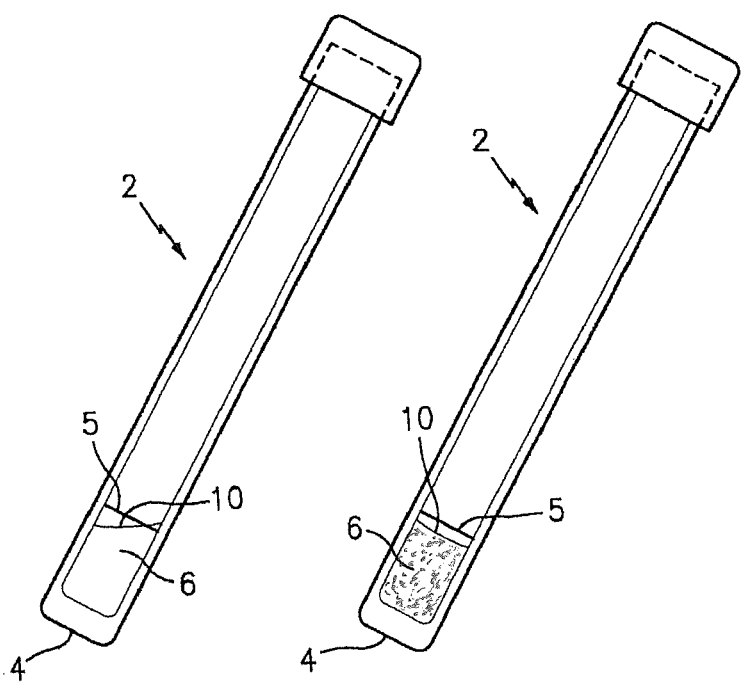
FIG. 5 is a side elevational view of a test tube after the specimen has been deposited and cultured in a present invention medium that is operable to clot in the presence of a targeted strain of antibiotic resistant strain of *P. staphylococci*, which view illustrates the absence of a clot and therefore the targeted bacteria in the specimen.
FIG. 6 is a side elevational view similar to FIG. 5, but showing the present test medium after the culturing period and indicating a clot and therefore the presence of the targeted *P. staphylococci* in the specimen.

FIG. 1 is a side elevational view of a test tube denoted by the numeral 2 which contains a sample test mixture 12 for use in performing the *P. staphylococci* presence/absence test of this invention. To simplify this Detailed Description of the present invention, the present invention is described below (unless otherwise noted) as applied to the MRSA strain of *P. staphylococci*. As indicated above, however, the present invention is not limited to the detection of MRSA and can be used to detect other *P. staphylococci*.

The tube 2 preferably has a flat bottom 4 and a top closure 3. The tube 2 contains a dry powdered test mixture 12 which is formed in accordance with an embodiment of this invention for detecting the presence or absence of a targeted antibiotic resistant strain of *P. staphylococci* (e.g., MRSA) in a sample; e.g., a first generational biological sample. The tube 2 is also provided with a reference line 5 which indicates the amount of hydrating liquid, preferably water, to be added to the tube 2 in order to properly hydrate the powdered mixture 12 for specimen sample testing.

An effective formulation for detecting the presence or absence of MRSA in a first generation sample of the type referred to herein is set forth below. The amounts of each ingredient in the formulation are found to be effective amounts thereof

| Constituent | Gms/L of Test Mixture | Range | Function |
| --- | --- | --- | --- |
| MuellerHinton Broth | 8.00 | 1.0-20.0 | protein source |
| Yeast Extract | 5.25 | 0.5-20.0 | vitamin source |
| Lithium Chloride | 5.0 | 1.0-10.0 | selective agent |
| Trehalose | 12.0 | 1.0-20.0 | source of carbon |
| Phenol red | 0.018 | 0.01-0.03 | pH indicator |
| Maltose | 3.0 | 0.05-10.0 | inducer sugar |
| Mannitol | 5.0 | 0.055-20.0 | second carbon source |
| Amphotericin B | 0.005 | 0.001-0.020 | anti-yeast selective agent |
| Kinetin | 0.001 | 0.001-0.010 | plant growth hormone |
| Indole butyric acid | 0.005 | 0.001-0.020 | plant growth hormone |
| Gibberellic acid | 0.001 | 0.0001-0.020 | plant growth hormone |
| IPTG | 0.005 | 0.0001-0.020 | inducer |
| Phenyl ethyl alcohol | 1.500 ml | 0.5 ml-10 ml | anti-gram negative |
| Desfuroxime | 0.0015 | 0.0005-0.0050 | selective inhibitor |
| Potassium phosphate | 0.500 | 0.10-5.0 | effervescent |
| Aztreonam | 0.020 | 0.005-0.050 | antibiotic |
| Kanamycin | 0.020 | 0.001-0.050 | selective antibiotic |
| Colistin | 0.005 | 0.0011-0.020 | antibiotic |
| Cefoxitin | 0.008 | 0.001-0.030 | selective antibiotic |
| Rabbit plasma | 50.00 | 10.0-100.0 | Coagulase substrate |
| Fibrinogen | 11.33 | 1.0-20.0 | Coagulase substrate |

Gentamicin and/or Tobramycin in an amount of 0.010 and in a range of 0.001-0.050 Gms/L can be substituted for Kanamycin in the above test medium formulation. This specific example does not represent all test medium formulations, and the present invention is not limited thereto. In particular, the test medium configured will be altered when used to detect strains of *P. staphylococci* other than MRSA. For example, in the above described medium example, mannitol and trehalose are included for selective detection of *S. aureus*. In alternative medium embodiments, this constituent could be replaced by an alternative selective ingredient specific to the alternative targeted bacteria. As stated above, those in the art will recognize that many different combinations of constituents, and varying effective amounts of the same, can be used to provide the same functionality. Hence, the present method and mixture contemplates that a number of different constituent formulations can be made. The above mixture preferably includes an effective amount of a protein source; an effective amount of a vitamin source; an effective amount of a carbon source; an effective amount of plant growth hormones; an effective amount of a pH indicator; and a selective amount of an antibiotic which, in this example, is directed against MSSA.

FIG. 2 shows three of the test tubes 2, 2', and 2" wherein the powdered mixture 12 has been properly hydrated by the addition of water, preferably distilled water, to form a hydrated test mixture 8. The tube 2 is the sampling tube to which a first generation specimen sample to be analyzed for the presence or absence of MRSA is added. The specimen sample, which can be a swab of the specimen being tested, is combined with the hydrated test mixture 8. The tubes 2' and 2" are tubes of the hydrated test mixture which are used as positive and negative controls for the test mixture. When performing the sample analyzation procedure, the sample being tested is added to the hydrated test mixture 8 in the tube 2, while a sample of MRSA is added to tube 2' and a sample of MSSA is added to tube 2". In the instant case, when the test mixture is hydrated, the hydrated solution has a particular color which can be red for example. In the example shown in the drawings the initial color is a dark color, such as red. FIG. 3 shows one result of the test after a predetermined incubation period which can be from eight to twenty four hours, for example. In the tube 2 in which the sample being analyzed was placed, there is no color change in the hydrated mixture 8, while in the positive control tube 2' to which the MRSA was added, the color of the hydrated mixture 8' has changed and become lighter. This is a confirmation of the presence of MRSA in the mixture 8' via a detectable signal; i.e., color. It will be noted also that the hydrated test mixture 8 in the tube 2" to which the MSSA was added did not change color. Thus the specimen tube 2 indicates no presence of MRSA while the tube 2' does and the tube 2" does not. Thus this test result indicates that the specimen sample being tested is free of MRSA. FIG. 4 indicates that the specimen being tested in the tube 2 does contain MRSA since the hydrated specimen sample test mixture changes to the color 8' which is the same as the color of the test mixture 8' in the positive control tube 2'. This color change indicates that the specimen sample does contain MRSA.

In addition to the above formulation, a control formulation which will rule out false positive results can be included in test kits for performing the analysis. The control formulation will be the same as that set forth above with the exception that it will not include an antibiotic such as Cefoxitin.

As noted above, the present medium may include growth inhibitors directed toward non-targeted strains of *P. staphylococci* (e.g., MSSA), which inhibitors function to inhibit or otherwise negatively affect growth of non-targeted bacteria, while not interfering with the growth of the targeted strain of *P. staphylococci* (e.g., MRSA). Examples of growth inhibitors that can be used to inhibit MSSA include, but are not limited to, cefoxitin, colistin, aztreonam, and anti-ribosomal amino glycoside antibiotics such as gentamicin, kanamycin, tobramycin, and sisomycin. Anti-ribosomal amino glycoside antibiotics can stop protein synthesis.

Referring to FIGS. 5 and 6, in those embodiments of the present invention that are operable to clot in the presence of the targeted strain of antibiotic resistant of *P. staphylococci*, after the inoculation period the container (e.g., test tube 2) holding the inoculated test mixture can be inspected for the presence of a clot; e.g., the test tube 2 can be tilted to one side as shown in FIGS. 5 and 6 to see if the meniscus 10 of the text mixture will move or whether a clot keeps the test mixture below a reference line 5. The presence of a clot indicates that the targeted *P. staphylococci* is present in the test sample (see FIG. 6), and the absence of a clot in the inoculated test mixture indicates that targeted *P. staphylococci* is not present in the test mixture 6 (see FIG. 5). In some instances, the entire inoculated test mixture will clot, and in others some liquid will remain in the container with the clot. In the embodiment of the present invention that produces both a sensible signal and a clot in the presence of the target *P. staphylococci*, the combination of the two characteristics (clot and color) facilitate the detection of the positive result and thereby increase the sensitivity of the test. In addition, the clot operates to enhance the coloration of the detectable signal (e.g., increasing intensity of yellow color) which further facilitates the determination. Approximately 80% of the present tests performed using first generation nasal samples clotted within six hours when *S. aureus* is present in the first generation test sample.

While the invention has been described with respect to preferred embodiments, those skilled in the art will readily appreciate that various changes and/or modifications can be made to the invention.

What is claimed is:

1. A method for detecting the presence or absence of a vancomycin-resistant *Staphylococcus aureus* (VRSA) in a test sample, the method comprising the steps of:
    providing a test medium having at least one hydrolysable substrate, which substrate is operable to promote the growth of the VRSA and to produce a detectable signal when the hydrolyzable substrate is metabolized by the VRSA and which test medium further includes one or more coagulase substrates operable to react with coagulase produced by the VRSA to produce a clot;
    forming a mixture of the test sample and hydrated test medium;
    incubating the mixture at temperatures in the range of about 20° C. to about 42° C.; and
    detecting the presence or absence of the VRSA in the test sample by the presence or absence of the detectable signal and the presence or absence of the clot in the mixture.

2. The method of claim 1, further comprising the step of collecting a first generational form of the test sample.

3. The method of claim 2, wherein the step of collecting the first generational sample includes swabbing one of: a tissue surface of a human subject, a tissue surface of an animal subject, an environmental surface, or a food sample.

4. The method of claim 1, wherein the hydrolyzable substrate includes one or more sugars that can be metabolized by the VRSA.

5. The method of claim 1, wherein the test medium further includes one or more growth inhibitors operable to inhibit the growth of pathogenic *staphylococci* strains other than VRSA.

6. The method of claim 1, wherein the test mixture includes plasma as a source of the coagulase substrates.

7. The method of claim 6, where the plasma is rabbit plasma.

8. The method of claim 1, wherein the test mixture includes fibrinogen as a source of coagulase substrates.

9. The method of claim 8, wherein the fibrinogen is bovine fibrinogen.

* * * * *